United States Patent
Bhai

(10) Patent No.: US 8,973,186 B2
(45) Date of Patent: Mar. 10, 2015

(54) OPTIMIZATION OF THE OPERATION OF A PATIENT-SUPPORT APPARATUS BASED ON PATIENT RESPONSE

(75) Inventor: Aziz A. Bhai, West Chester, OH (US)

(73) Assignee: Hill-Rom Services, Inc., Batesville, IN (US)

(*) Notice: Subject to any disclaimer, the term of this patent is extended or adjusted under 35 U.S.C. 154(b) by 445 days.

(21) Appl. No.: 13/314,669

(22) Filed: Dec. 8, 2011

(65) Prior Publication Data

US 2013/0145558 A1 Jun. 13, 2013

(51) Int. Cl.
 *A61G 7/00* (2006.01)

(52) U.S. Cl.
 USPC ........................................ 5/600; 5/613; 5/616

(58) Field of Classification Search
 USPC ........... 5/600, 613, 616–618, 710, 713, 655.3
 See application file for complete search history.

(56) References Cited

U.S. PATENT DOCUMENTS

| | | |
|---|---|---|
| 779,576 A | 1/1905 | Berryman |
| 1,772,310 A | 8/1930 | Hart |
| 3,303,518 A | 2/1967 | Ingram |
| 3,462,778 A | 8/1969 | Whitney |
| 3,674,019 A | 7/1972 | Grant |
| 3,678,520 A | 7/1972 | Evans |
| 3,772,717 A | 11/1973 | Yuen et al. |
| 3,879,776 A | 4/1975 | Solen |
| 3,882,425 A | 5/1975 | Briley |
| 3,978,530 A | 9/1976 | Amarantos |
| 4,015,928 A | 4/1977 | Carlson |
| 4,042,988 A | 8/1977 | Holliday |
| 4,120,278 A | 10/1978 | Ward |
| 4,150,654 A | 4/1979 | Heitzman et al. |
| 4,193,149 A | 3/1980 | Welch |
| 4,220,312 A | 9/1980 | Pauliukonis |
| 4,225,989 A | 10/1980 | Corbett et al. |
| 4,267,611 A | 5/1981 | Agulnick |
| 4,336,621 A | 6/1982 | Schwartz et al. |
| 4,391,009 A | 7/1983 | Schild et al. |
| 4,472,847 A | 9/1984 | Gammons et al. |
| 4,477,935 A | 10/1984 | Griffin |
| 4,483,029 A | 11/1984 | Paul |
| 4,525,885 A | 7/1985 | Hunt et al. |
| 4,527,298 A | 7/1985 | Moulton |
| 4,527,715 A | 7/1985 | Rosenbaum |
| 4,541,135 A | 9/1985 | Karpov |
| 4,637,083 A | 1/1987 | Goodwin |

(Continued)

FOREIGN PATENT DOCUMENTS

| | | |
|---|---|---|
| CA | 2 393 880 | 1/2004 |
| DE | 103 16 162 A1 | 10/2004 |

(Continued)

OTHER PUBLICATIONS

Renaissance™, Therapeutic Mattress Replacement System, Pegausus Airwave Inc., date unknown.

(Continued)

*Primary Examiner* — Nicholas Polito
(74) *Attorney, Agent, or Firm* — Barnes & Thornburg LLP

(57) ABSTRACT

A patient-support apparatus according the present disclosure includes a source of pressurized air, a plurality of bladders, a plurality of pressure sensors, and a controller. The controller is configured to execute instructions to adjust pressures in the bladders based on information from the plurality of pressure sensors.

22 Claims, 10 Drawing Sheets

(56) References Cited

U.S. PATENT DOCUMENTS

| | | | |
|---|---|---|---|
| 4,638,519 A | 1/1987 | Hess | |
| 4,639,960 A | 2/1987 | Guillen et al. | |
| 4,679,264 A | 7/1987 | Mollura | |
| 4,685,163 A | 8/1987 | Guillen et al. | |
| 4,803,744 A | 2/1989 | Peck et al. | |
| 4,807,313 A | 2/1989 | Ryder et al. | |
| 4,825,486 A | 5/1989 | Kimura et al. | |
| 4,833,461 A | 5/1989 | Yeager | |
| 4,839,512 A | 6/1989 | Speck | |
| 4,904,830 A | 2/1990 | Rizzuto | |
| 4,934,468 A | 6/1990 | Koerber, Sr. et al. | |
| 4,940,861 A | 7/1990 | Rizzuto | |
| 4,944,060 A | 7/1990 | Peery et al. | |
| 4,951,335 A | 8/1990 | Eady | |
| 4,953,244 A | 9/1990 | Koerber, Sr. et al. | |
| 4,953,247 A | 9/1990 | Hasty | |
| 4,989,283 A * | 2/1991 | Krouskop | 5/713 |
| 4,993,920 A | 2/1991 | Harkleroad et al. | |
| 4,995,124 A | 2/1991 | Wridge, Jr. et al. | |
| 5,020,176 A | 6/1991 | Dotson | |
| 5,029,352 A | 7/1991 | Hargest et al. | |
| 5,036,559 A * | 8/1991 | Hargest | 5/689 |
| 5,060,174 A | 10/1991 | Gross | |
| 5,067,189 A | 11/1991 | Weedling et al. | |
| 5,117,518 A | 6/1992 | Schild | |
| 5,121,512 A | 6/1992 | Kaufmann | |
| 5,129,115 A | 7/1992 | Higgins et al. | |
| 5,140,309 A | 8/1992 | Gusakov | |
| 5,163,196 A | 11/1992 | Graebe et al. | |
| 5,168,589 A | 12/1992 | Stroh et al. | |
| 5,170,364 A | 12/1992 | Gross et al. | |
| 5,179,920 A | 1/1993 | Bender | |
| 5,183,518 A | 2/1993 | Radon | |
| 5,184,122 A | 2/1993 | Decious et al. | |
| 5,189,742 A | 3/1993 | Schild | |
| 5,243,723 A | 9/1993 | Cotner et al. | |
| 5,249,318 A | 10/1993 | Loadsman | |
| 5,251,349 A | 10/1993 | Thomas et al. | |
| 5,269,030 A | 12/1993 | Pahno et al. | |
| 5,276,432 A | 1/1994 | Travis | |
| 5,325,551 A | 7/1994 | Tappel et al. | |
| 5,364,162 A | 11/1994 | Bar et al. | |
| 5,394,577 A | 3/1995 | James et al. | |
| 5,396,671 A | 3/1995 | Stacy | |
| 5,421,044 A | 6/1995 | Steensen | |
| 5,483,709 A | 1/1996 | Foster et al. | |
| 5,483,711 A | 1/1996 | Hargest et al. | |
| 5,539,942 A | 7/1996 | Melou | |
| 5,561,873 A | 10/1996 | Weedling | |
| 5,561,875 A | 10/1996 | Graebe | |
| 5,564,142 A | 10/1996 | Liu | |
| 5,586,346 A | 12/1996 | Stacy et al. | |
| 5,596,781 A | 1/1997 | Graebe | |
| 5,611,096 A | 3/1997 | Bartlett et al. | |
| 5,611,772 A | 3/1997 | Fujimoto et al. | |
| 5,619,764 A | 4/1997 | Lopau | |
| 5,623,736 A | 4/1997 | Soltani et al. | |
| 5,634,224 A | 6/1997 | Gates | |
| 5,634,225 A | 6/1997 | Miller, Sr. et al. | |
| 5,651,153 A | 7/1997 | Goodrich | |
| 5,680,036 A | 10/1997 | Faulk | |
| D386,035 S | 11/1997 | Matsler et al. | |
| 5,684,460 A | 11/1997 | Scanlon | |
| 5,689,845 A | 11/1997 | Sobieralski | |
| 5,699,570 A | 12/1997 | Wilkinson et al. | |
| 5,701,622 A | 12/1997 | Biggie et al. | |
| 5,745,942 A | 5/1998 | Wilkerson | |
| 5,765,246 A | 6/1998 | Shoenhair | |
| 5,774,917 A | 7/1998 | Liu | |
| 5,787,531 A | 8/1998 | Pepe | |
| 5,794,288 A | 8/1998 | Soltani et al. | |
| 5,806,572 A | 9/1998 | Voller | |
| 5,815,864 A | 10/1998 | Sloop | |
| 5,815,865 A | 10/1998 | Washburn et al. | |
| 5,829,081 A | 11/1998 | Pearce | |
| 5,845,352 A | 12/1998 | Matsler et al. | |
| 5,873,137 A * | 2/1999 | Yavets-Chen | 5/713 |
| D407,353 S | 3/1999 | Bar et al. | |
| D408,767 S | 4/1999 | Bar et al. | |
| 5,890,245 A | 4/1999 | Klearman et al. | |
| 5,917,180 A | 6/1999 | Reimer et al. | |
| D412,685 S | 8/1999 | Bar et al. | |
| D413,085 S | 8/1999 | Bar et al. | |
| D413,841 S | 9/1999 | Bar et al. | |
| 5,954,402 A | 9/1999 | McInturff | |
| D415,567 S | 10/1999 | Bar | |
| D415,834 S | 10/1999 | Bar | |
| 5,970,789 A | 10/1999 | Meyer et al. | |
| D416,326 S | 11/1999 | Bar | |
| 5,984,418 A | 11/1999 | McInturff | |
| 6,009,580 A | 1/2000 | Caminade et al. | |
| 6,014,346 A | 1/2000 | Malone | |
| 6,021,800 A | 2/2000 | Schild et al. | |
| 6,058,538 A | 5/2000 | Chapman et al. | |
| 6,094,762 A | 8/2000 | Viard et al. | |
| 6,095,611 A | 8/2000 | Bar et al. | |
| 6,098,222 A | 8/2000 | Hand et al. | |
| 6,134,732 A | 10/2000 | Chapman et al. | |
| 6,145,142 A | 11/2000 | Rechin et al. | |
| 6,148,461 A | 11/2000 | Cook et al. | |
| 6,165,142 A | 12/2000 | Bar | |
| D439,098 S | 3/2001 | Matsler et al. | |
| 6,212,718 B1 | 4/2001 | Stolpmann et al. | |
| D446,674 S | 8/2001 | Chapman et al. | |
| 6,280,392 B1 | 8/2001 | Yoshimi et al. | |
| 6,349,439 B1 | 2/2002 | Cook et al. | |
| 6,353,950 B1 | 3/2002 | Bartlett et al. | |
| 6,385,804 B1 | 5/2002 | Barber et al. | |
| 6,412,129 B1 | 7/2002 | Wu | |
| D463,701 S | 10/2002 | Gorcherding et al. | |
| 6,474,743 B1 | 11/2002 | Harker et al. | |
| 6,487,739 B1 | 12/2002 | Harker | |
| 6,560,804 B2 | 5/2003 | Wise et al. | |
| 6,564,410 B2 | 5/2003 | Graebe et al. | |
| 6,568,273 B2 | 5/2003 | Reimer | |
| 6,593,588 B1 | 7/2003 | Reimer | |
| 6,623,080 B2 | 9/2003 | Clapper | |
| 6,646,556 B1 | 11/2003 | Smith et al. | |
| 6,686,711 B2 | 2/2004 | Rose et al. | |
| 6,687,936 B2 | 2/2004 | Graebe et al. | |
| 6,687,937 B2 | 2/2004 | Harker | |
| 6,701,556 B2 | 3/2004 | Romano et al. | |
| 6,701,558 B2 | 3/2004 | VanSteenburg | |
| 6,721,980 B1 | 4/2004 | Price et al. | |
| 6,848,135 B1 | 2/2005 | Kohlman | |
| 6,877,178 B2 | 4/2005 | Chapman et al. | |
| 6,892,405 B1 | 5/2005 | Dimitriu et al. | |
| 6,987,232 B2 | 1/2006 | Smith et al. | |
| 7,145,461 B2 | 12/2006 | Lehrman et al. | |
| 7,251,845 B2 * | 8/2007 | Schaller et al. | 5/613 |
| 7,311,675 B2 * | 12/2007 | Peifer et al. | 600/587 |
| 7,506,390 B2 | 3/2009 | Dixon et al. | |
| 7,747,688 B2 | 6/2010 | Narayanaswami et al. | |
| 8,090,478 B2 | 1/2012 | Skinner et al. | |
| 2005/0172398 A1 | 8/2005 | Smith et al. | |
| 2006/0152378 A1 | 7/2006 | Lokhorst et al. | |
| 2008/0189865 A1 | 8/2008 | Bhai | |
| 2009/0003522 A1 * | 1/2009 | Chien et al. | 378/65 |
| 2010/0101022 A1 | 4/2010 | Riley | |
| 2010/0122415 A1 | 5/2010 | Turner et al. | |
| 2011/0197366 A1 * | 8/2011 | Lachenbruch | 5/655.3 |
| 2012/0174322 A1 | 7/2012 | Skinner et al. | |
| 2012/0194436 A1 | 8/2012 | Thodupunuri et al. | |

FOREIGN PATENT DOCUMENTS

| | | |
|---|---|---|
| DE | 103 33 742 A1 | 2/2005 |
| EP | 0 403 186 A2 | 12/1990 |
| EP | 0 560 563 A1 | 9/1993 |
| EP | 0 853 918 A2 | 7/1998 |
| EP | 2 359 791 A2 | 8/2011 |
| EP | 2 508 128 A1 | 10/2012 |
| FR | 2 757 377 | 6/1998 |
| FR | 2 814 062 | 3/2002 |

(56) References Cited

FOREIGN PATENT DOCUMENTS

| | | |
|---|---|---|
| GB | 159299 | 2/1921 |
| GB | 959103 | 5/1964 |
| GB | 2 090 734 | 7/1982 |
| GB | 2 092 439 A | 8/1982 |
| GB | 2 167 293 A | 5/1986 |
| GB | 2 197 192 A | 5/1988 |
| GB | 2 199 803 A | 7/1988 |
| GB | 2 267 217 A | 12/1993 |
| GB | 2 307 402 A | 5/1997 |
| WO | WO 94/09686 | 5/1984 |
| WO | WO 86/02244 | 4/1986 |
| WO | WO 86/05973 | 10/1986 |
| WO | WO 95/31920 | 11/1995 |
| WO | WO 96/33641 | 10/1996 |
| WO | WO 97/17869 | 5/1997 |
| WO | WO 98/24345 | 6/1998 |
| WO | WO 99/39613 | 8/1999 |
| WO | WO 01/09695 A1 | 2/2001 |
| WO | WO 01/74287 A1 | 10/2001 |
| WO | WO 02/45641 A1 | 6/2002 |
| WO | WO 2004/006768 | 1/2004 |
| WO | WO 2005/013878 | 2/2005 |

OTHER PUBLICATIONS

A Hill-Rom solution, Acucaire Continuous Airflow System, date unknown.
Air Flow 500 Mattress Replacement System, Atlantis Medical, Milltown, NJ, date unknown.
Apropos, CRS-8500, National Patient Care Systems, date unknown.
ASAP II Therapy System, DynaMedics Corporation, London, ON, Canada, Mar. 1995.
Bazooka, Innovative Medical System, Manchester, NH, 1995.
DFS® Homecare Advanced Dynamic Flotation System, HNE Healthcare, Manalapan, NJ, date unknown.
Economic Relief, Bio Therapy® Plus, Sunrise Medical Bio Clinic, Ontario, CA, date unknown.
First Step, Mattress Replacement System, KCI, San Antonio, TX, 1991.
Gaymar Sof-Care Plus © CompanionO System, Gaymar Industries, Inc., 1994.
Hill-Rom PrimeAire ARS Pressure Relief Mattress, date unknown.
Impression, Pressure Relief Therapy, KCI, date unknown.
Lumex AkroTech 4000, Lumex, date unknown.
microAlR 1000, GSI Medical Systems, Carmel, NY, 1989.
Pro 2000 MRS, Pneu-Care Series, Cardio Systems, Dallas, TX, date unknown.
Prodigy Mattress Crown Theraputics, Inc., date unknown.
Roho Dry Flotation Isolette see roho.com/medical/isolette.jsp, date unknown.
Roho series Crown Therapautic, Inc. See woundheal.com, date unknown.
Tytex Group AirX #D Spacer Fabric see tytex.cms.digitalis.dk, date unknown.
Extended European Search Report for EP 12 19 5522.3, dated Nov. 11, 2013, 8 pages.

\* cited by examiner

OPTIMIZATION OF THE OPERATION OF A PATIENT-SUPPORT APPARATUS BASED ON PATIENT RESPONSE

BACKGROUND

The present disclosure is related to the arrangement and operation of a patient-support apparatus with sensors for gathering information about a patient supported on the patient-support apparatus. More specifically, the present disclosure is related to a patient-support apparatus including sensors for determining movement of a patient supported on the patient-support apparatus and reconfiguring operation of the patient-support apparatus in response to movement of the patient.

Patient-support apparatuses, such as hospital beds, sometimes include mattresses and frames for supporting the mattresses. Some mattresses may include inflatable bladders for supporting patients lying on the support surfaces at different pressures. Some frames may be movable so that a support surface positioned on the frame can be moved between a flat configuration and a number of inclined configurations for supporting a patient sitting up on the patient-support apparatus.

Patient-support apparatuses are used in hospitals, nursing homes, private homes, and the like. Patients supported on patient-support apparatuses are known to migrate over time toward a foot end of the patient-support apparatus. Caregivers are sometimes tasked with repositioning patients on patient-support apparatuses when the patient migrates too far toward the foot end of the patient-support apparatus.

SUMMARY

The present invention comprises one or more of the features recited in the appended claims and/or the following features which, alone or in any combination, may comprise patentable subject matter.

The present invention includes a patient-support apparatus having a head end and a foot end. The patient-support apparatus includes a source of pressurized air, a plurality of bladders, a manifold, a plurality of pressure sensors, and a controller. The manifold is in communication with the source of pressurized air and with the plurality of bladders. The manifold is also configured to control the flow of air between the source of pressurized air and the plurality of bladders. The plurality of pressure sensors are in fluid communication with the plurality of bladders and produce pressure signals indicative of air pressure within each of the plurality of bladders. The controller is in electrical communication with the source of pressurized air, the manifold, and the plurality of pressure sensors. The controller includes a processor, a timer coupled to the processor, and a memory device coupled to the processor. The memory device has stored therein a plurality of instructions. When the plurality of instructions are executed by the processor, the processor retrieves a baseline patient-specific profile including at least one patient factor from the memory, calculates an expected first patient outcome, calculates a set of patient-specific operating parameters based on the patient-specific profile, wherein the set of operating parameters includes a set of target pressures for the plurality of bladders, measures an actual first patient outcome, optimizes the set of target pressures based on the differences between the actual first patient outcome and the expected first patient outcome, updates the baseline patient-specific profile to include the first patient outcome, and adjusts the pressures in the bladders to the target pressures.

In some embodiments, the first outcome may be an amount of patient migration toward the foot end of the bed. The processor may execute an addition instruction to compare the first patient outcome to an expected range of patient outcome values corresponding to patient migration.

The processor may determine a list of likely reasons based on the patient-specific profile when the first patient outcome is not equal to an expected patient outcome value. The patient-support apparatus may further include a user interface including a display and an input coupled to the controller. The processor may display the likely reasons on the display of the user interface. The processor may receive a selected reason corresponding to the first patient outcome from the likely reasons via the input and may update the patient-specific profile to include the selected reason.

The processor may calculate a second patient outcome over time. The processor may update the patient-specific profile to include the second patient outcome. The patient-support apparatus may include a user interface including a display and an input coupled to the controller. The processor may compare the second outcome to an expected range of patient outcome values, determine a list of likely reasons based on the patient-specific profile when an the first patient outcome is not equal to an expected patient outcome value, and display the likely reasons on the display of the user interface. The processor may receive a selected reason corresponding to the second patient outcome from the likely reasons via the input and may update the patient-specific profile to include the selected reason.

In another embodiment a patient-support apparatus having a head end and a foot end may include a source of pressurized air, a plurality of bladders, a manifold, a plurality of pressure sensors, and a controller. The manifold may be in communication with the source of pressurized air and with the plurality of bladders. The manifold may also be configured to control the flow of air between the source of pressurized air and the plurality of bladders. The plurality of pressure sensors may be in fluid communication with the plurality of bladders and may produce pressure signals indicative of air pressure within each of the plurality of bladders. The controller may be in electrical communication with the source of pressurized air, the plurality of valves, and the plurality of pressure sensors. The controller may include a processor, a timer coupled to the processor, and a memory device coupled to the processor. The memory device may have stored therein a plurality of instructions. The instructions may be executed by the processor so that the processor iteratively calculates a first patient outcome corresponding to the amount of migration of a patient toward the foot end of the bed over time, updates a baseline patient-specific profile to include the first patient outcome, calculates a set of operating parameters based on the updated patient-specific profile, wherein the set of operating parameters includes a first set of target pressures for the plurality of bladders, adjusts the pressures in the bladders to the first set of target pressures, and sets the updated patient-specific profile as the baseline patient-specific profile.

In some embodiments, the patient-support apparatus may also include a deck movable between a first configuration and a second configuration. The operating parameters may include a second set of target pressures for the plurality of bladders. The processor may adjust the pressures in the bladders to the first set of target pressures when the deck is in the first configuration and adjust the pressures in the bladders to the second set of target pressures when the deck is in the second configuration.

It is contemplated that the calculated operating parameters may include a parameter set to allow or to prevent movement of the deck from the first configuration to the second configuration. The patient-support apparatus may also include a transceiver coupled to the controller. The processor may transmit the patient-specific profile and the operating parameters via the transceiver.

In some embodiments, the patient-support apparatus may also include a transceiver coupled to the controller. The processor may receive an algorithm for calculating the operating parameters based on the patient-specific profile via the transceiver.

In some embodiments, the patient-support apparatus may also include a transceiver coupled to the controller and configured to communicate with a hospital information system. The processor may send the base patient-specific profile, the determined patient movement, and the caregiver response to the hospital information system via the transceiver. The processor may send the updated patient-specific profile to the hospital information system via the transceiver.

In some embodiments, during a first iteration of the instructions, the processor may retrieve the baseline patient-specific profile from the memory. The patient-specific profile may include information corresponding to at least one of patient age, patient weight, patient height, and patient sex.

According to another aspect of the present disclosure, a data analysis system may include a hospital network including at least one patient-support apparatus and a central information center. The central information center may be in communication with the patient-support apparatus. The central information center may be configured to receive data generated by the at least one patient-support apparatus corresponding to patient-specific profiles, calculated patient outcomes, and operating parameters of the at least one patient-support apparatus, determine operating parameters effective for modifying the calculated patient outcomes generated by the at least one patient-support apparatus, and generate an algorithm for calculating updated operating parameters of the at least one patient-support apparatus based on data corresponding to patient-specific profiles.

In some embodiments, the central information center is configured to determine interactions of data corresponding to a number of calculated patient outcomes. The central information center may be configured to transmit the algorithm for reception by the at least one patient-support apparatus.

The hospital network may include a hospital information system in communication with the at least one patient-support apparatus and the central information center. The hospital information system may be configured to receive data generated by the at least one patient-support apparatus corresponding to patient-specific profiles, calculated patient outcomes, and operating parameters of the at least one patient-support apparatus and generate a report including data corresponding to the calculated patient outcomes.

In some embodiments, the patient-support apparatus may have a head end and a foot end. The data generated by the at least one patient-support apparatus may correspond to a calculated amount of patient migration toward the foot end of the at least one patient-support apparatus over a predetermined amount of time. The patient-support apparatus may include a number of inflatable bladders and a number of pressure sensors coupled to the inflatable bladders. The number of pressure sensors may be configured to provide pressure information. The calculated amount of patient migration toward the foot end of the at least one patient-support apparatus may be determined based on pressure information from the pressure sensors.

The patient-support apparatus may include a number of inflatable bladders. The operating parameters effective for modifying the calculated patient outcomes may be determined by the central information center includes a target pressure for at least one of the number of inflatable bladders. It is contemplated that the data generated by the at least one patient-support apparatus may correspond to a patient weight.

DETAILED DESCRIPTION

Figure 1:
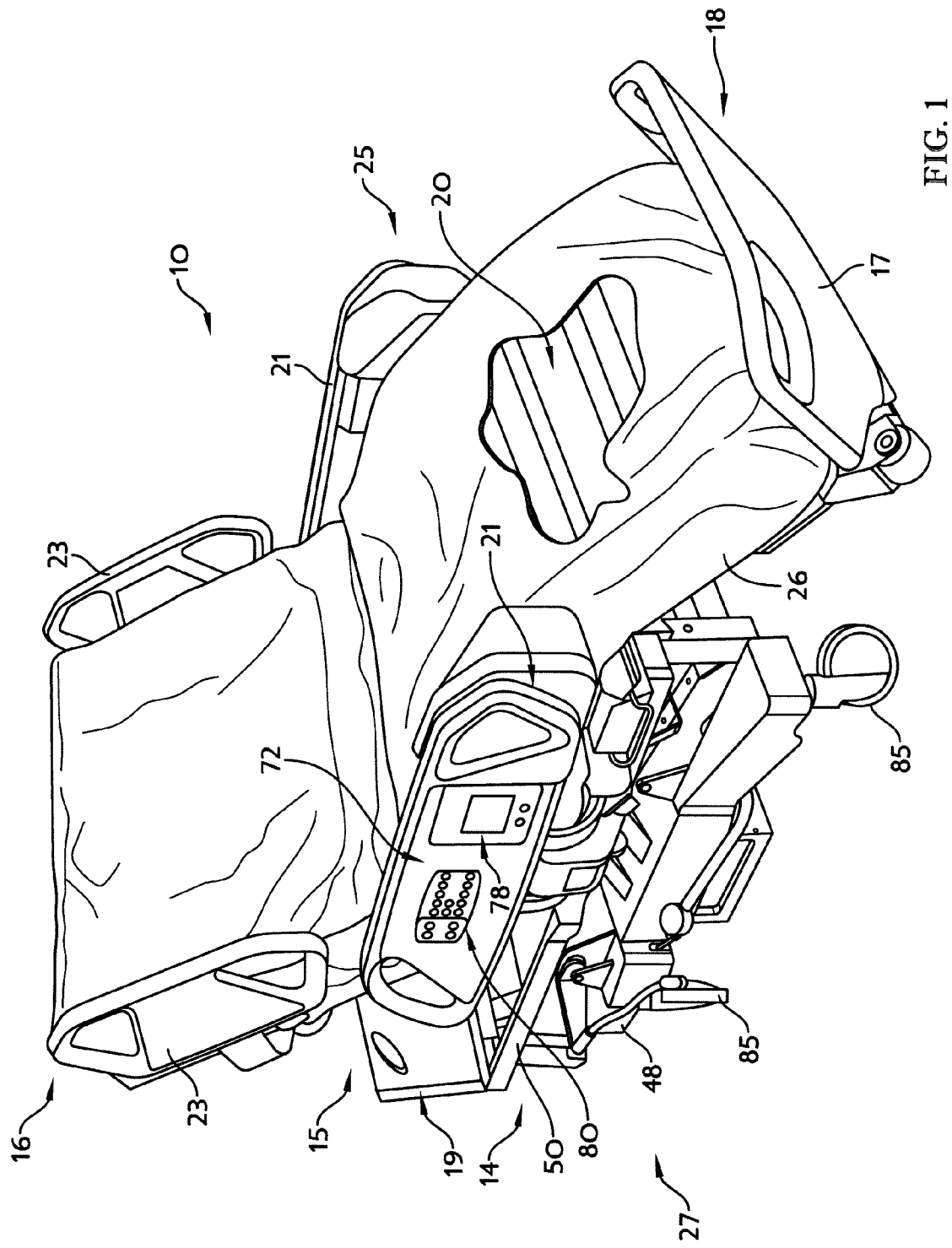
FIG. 1 is a perspective view of a patient-support apparatus including a frame and a mattress supported on the frame, the patient-support apparatus configured to measure migration of a patient supported on the mattress toward the foot end of the patient-support apparatus over time and to adjust the operating parameters of the patient-support apparatus to minimize the migration.
Figure 2:
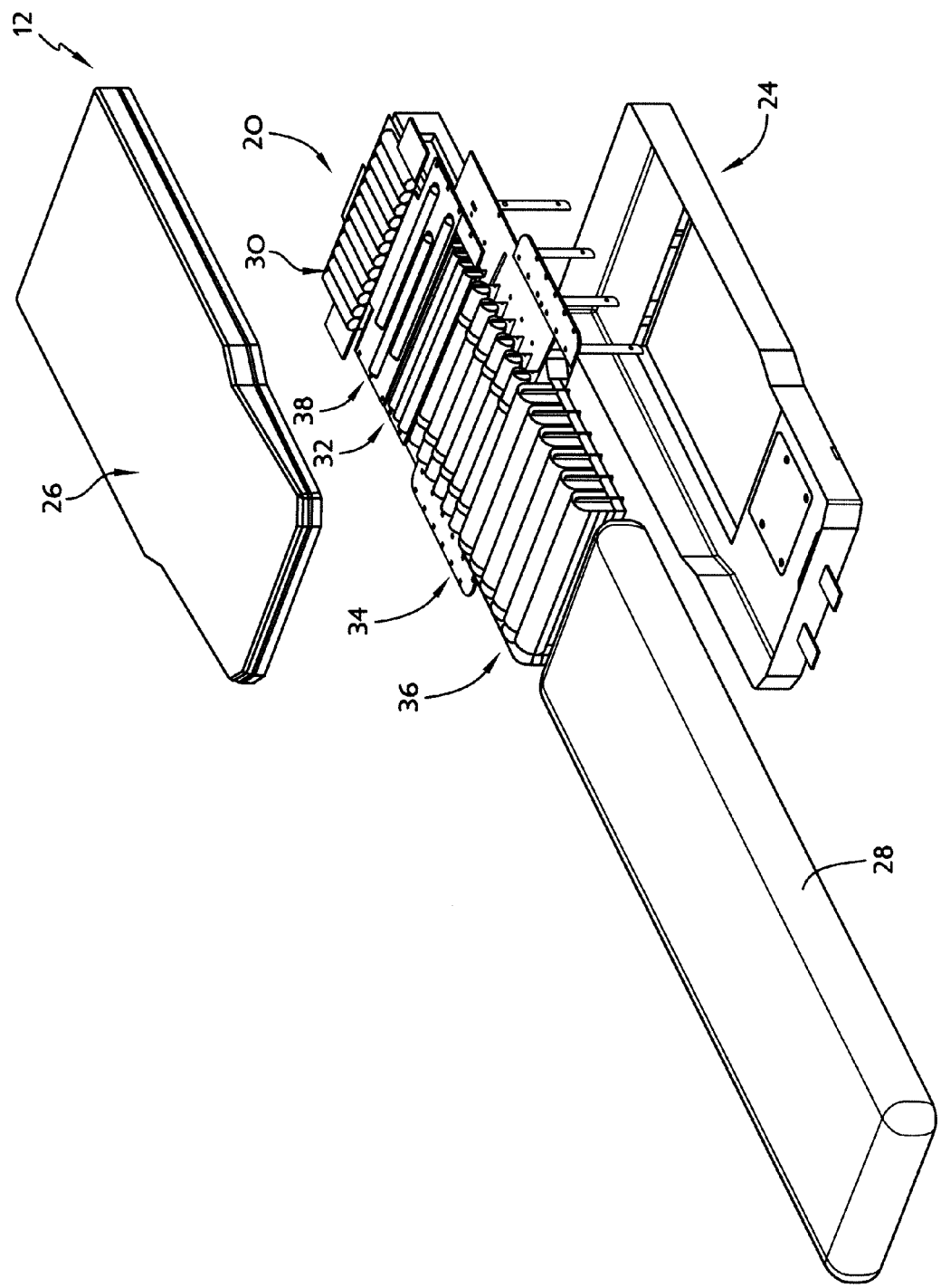
FIG. 2 is a partially exploded view of the support surface of FIG. 1 showing that the mattress includes a lower cover, a coverlet, a fire barrier, and a bladder assembly.
Figure 3:
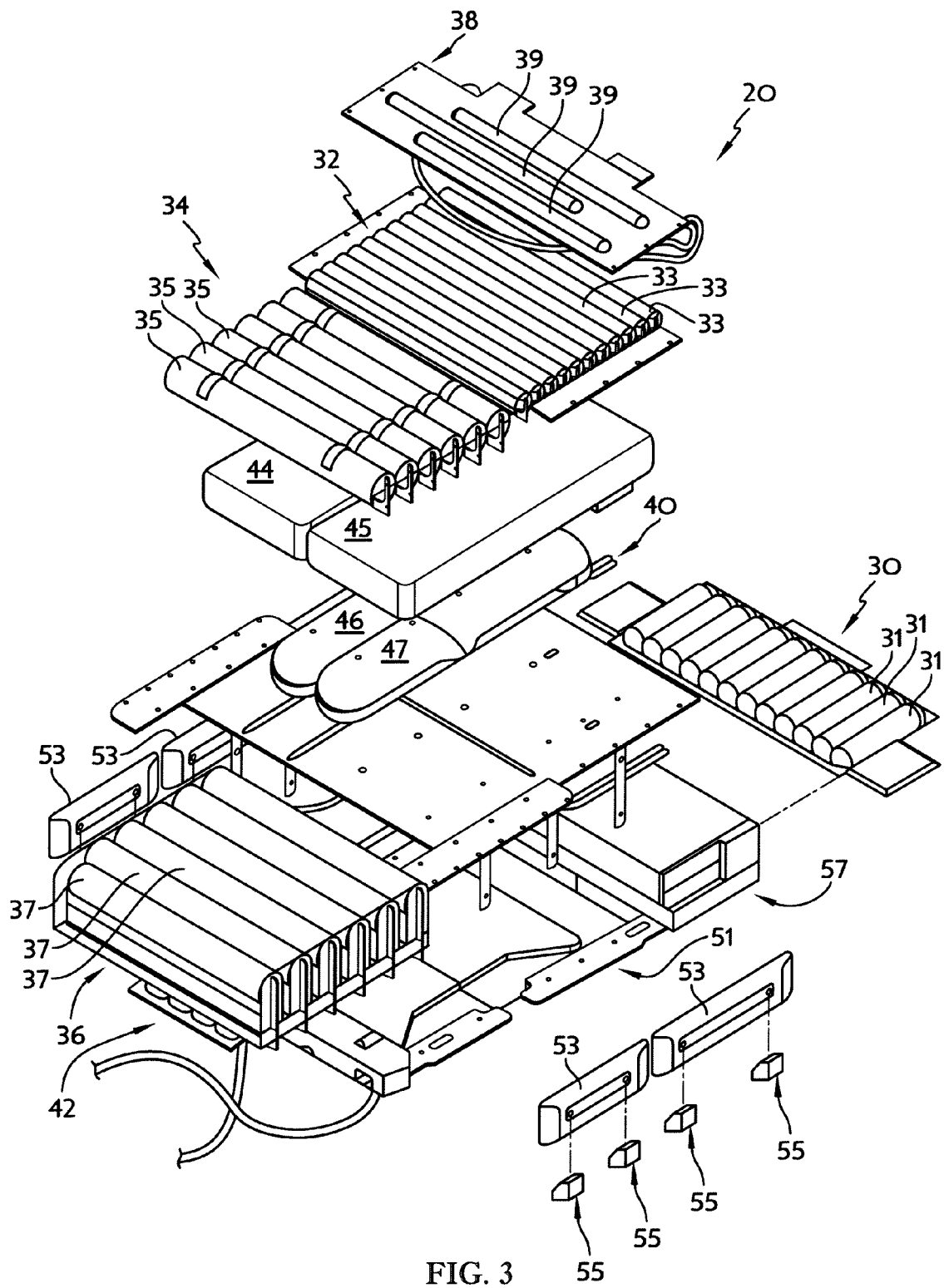
FIG. 3 is an exploded view of the bladder assembly of the mattress shown in FIG. 2.
Figure 4:
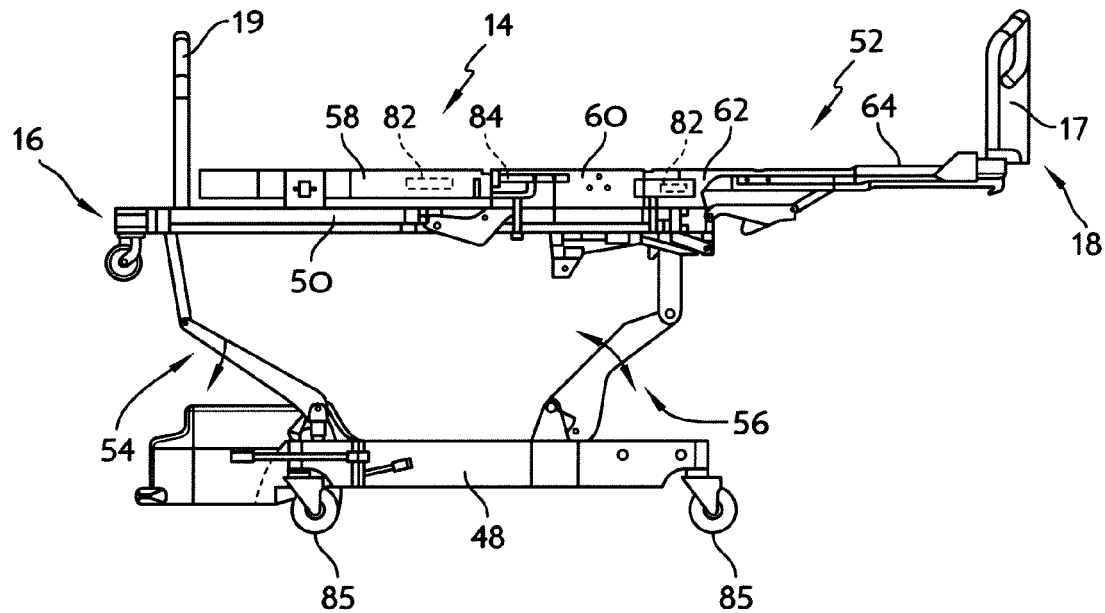
FIG. 4 is a side elevation view of the frame of FIG. 1 moved to a flat configuration.
Figure 5:
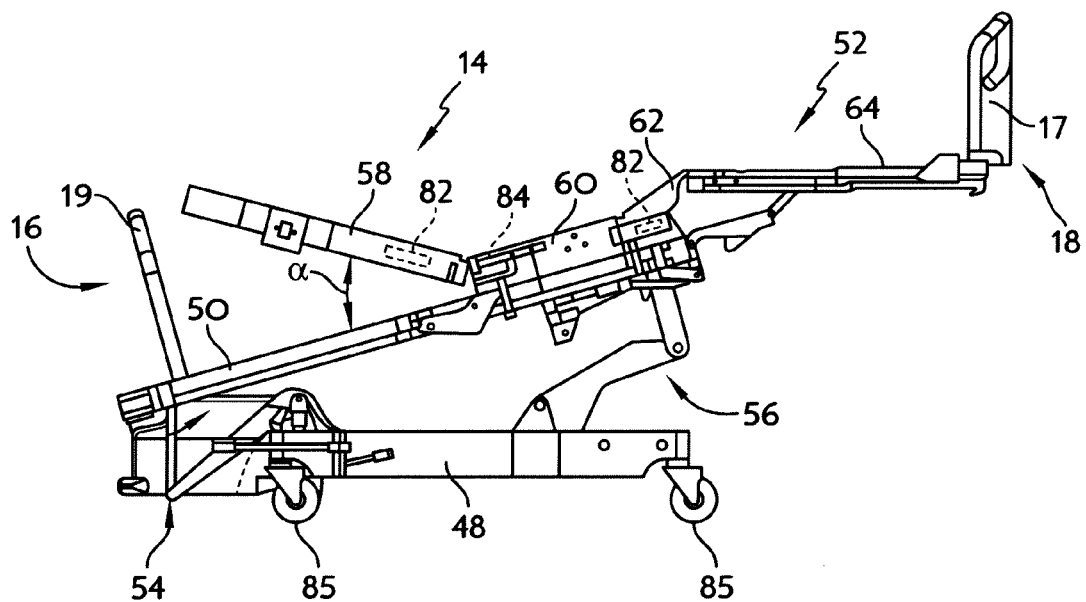
FIG. 5 is a side elevation view of the frame of FIG. 4 showing that a deck of the frame can be moved to other configurations to support a mattress in a number of arrangements as shown in FIG. 1.

A patient-support apparatus such as a hospital bed 10, for example, includes a mattress 12 and a frame 14 as shown in FIG. 1. The hospital bed 10 has a head end 16 and a foot end 18. The mattress 12 is supported on the frame 14. In the illustrative embodiment, the hospital bed 10 is a TotalCare® bed marketed by Hill-Rom Company, Inc. The mattress 12 includes an air bladder assembly 20, as shown in FIGS. 2 and 3, that is inflated and deflated to change the pressure profile of the mattress 12 when the mattress 12 is supporting a patient lying on the bed 10. The frame 14 is movable between a flat configuration, as shown in FIG. 4, and a number of inclined configurations for supporting a patient in a sitting-up or other position, one of which is shown in FIG. 5. In other embodiments, a patient-support apparatus may be just a mattress with a control system, a frame with a control system, or another device for supporting a patient.

Figure 6:
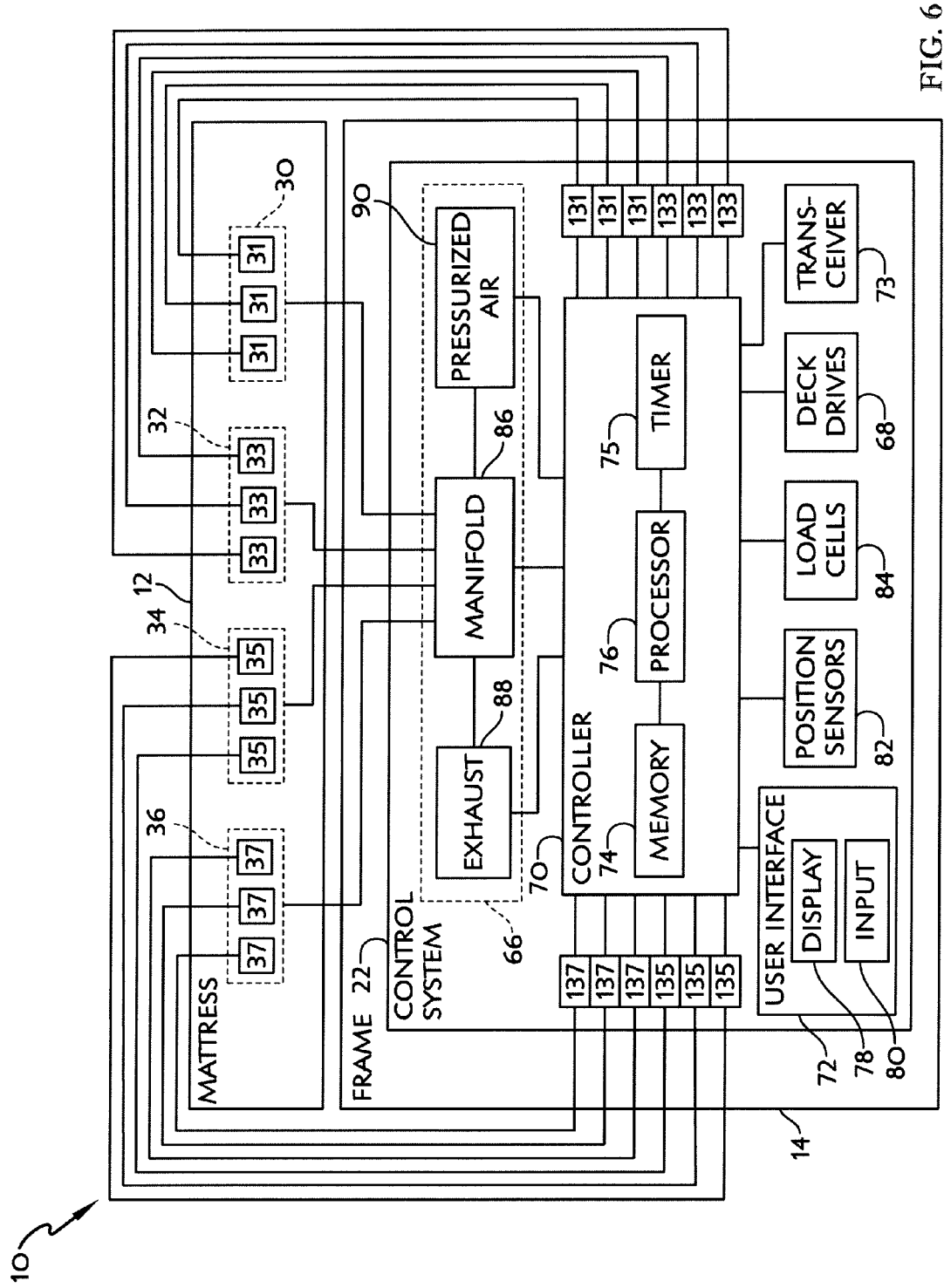
FIG. 6 is a diagrammatic view of the patient-support apparatus of FIG. 1 showing that the patient-support apparatus includes a control system.

The bed 10 includes a control system 22 as shown diagrammatically in FIG. 6. The control system 22 is configured to receive information about a patient supported on the bed 10 from sensors in the bed 10 and to create a patient-specific profile corresponding to the patient supported on the bed 10. The control system 22 is configured to update the patient-specific profile corresponding to the patient and to adjust the pressure in the in the air bladder assembly 20 based on the updated patient-specific profile to optimize a patient outcome. In particular, the illustrative control system 22 performs a control routine 200 to reduce migration of the patient toward the foot end 18 of the bed 10 and to modify operation of the bed 10 to optimize other patient outcomes such as patient restlessness and patient mobility.

In addition to the mattress 12 and the frame 14, the bed 10 illustratively includes a number of barriers 15 coupled to the frame 14 and a number of wheels 85 supporting the frame 14 as shown in FIG. 1. The barriers 15 illustratively include a footboard 17, a headboard 19, a pair of siderails 21, and a pair of headrails 23. The footboard 17 is located at the foot end 18 of the bed 10. The headboard 19 is located at the head end 16 of the bed 10. The siderails 21 extend along sides 25, 27 of the bed 10 and are movable between a blocking position extending above the mattress 12 and an exit position lower than the blocking position and configured to allow a patient to enter or exit the bed 10. The headrails 23 are located along the sides 25, 27 of the bed 10 near the head end 16 of the bed 10.

Referring now to FIG. 2, the mattress 12 illustratively includes a lower cover 24, a coverlet 26, a heat barrier 28, and the air bladder assembly 20. The lower cover 24 receives the air bladder assembly 20. The coverlet 26 couples to the lower cover 24 via a zipper (not shown) to enclose the air bladder assembly 20 when the mattress 12 is assembled. The heat barrier 28 surrounds the air bladder assembly 20 when the air bladder assembly 20 is enclosed by the coverlet 26.

The air bladder assembly 20 includes a head cushion 30, a torso cushion 32, a seat cushion 34, and a foot cushion 36 as shown in FIG. 2. The head cushion 30 includes a number of inflatable bladders 31 that extend longitudinally along the length of the mattress 12. The torso cushion 32 includes a number of inflatable bladders 33 that extend laterally across the mattress 12 between the sides 25, 27 of the bed 10. The seat cushion 34 includes a number of inflatable bladders 35 that extend laterally across the mattress 12. The foot cushion 36 includes a number of inflatable bladders 37 that extend laterally across the mattress 12. The bladders 31, 33, 35, 37 are independently inflatable and deflatable so that the pressure along the mattress 12 can be controlled to produce specific pressure profiles.

Different pressure profiles of the bladders 31, 33, 35, 37 can be produced in an effort to induce different patient outcomes. In one example, to mitigate or reverse patient migration toward the foot end 18 of the bed 10, the inflatable bladders 35 of the seat section 34 may be inflated to form a wedge or a dynamic wave as described in U.S. application Ser. No. 13/314,501 published as U.S. Pub. No. 2013/0145552 A1, herein incorporated by reference. In other examples, the pressure profile of the bladders may produce other shapes or desired interface pressures along the patient to achieve other patient outcomes.

Referring to FIG. 3, the air bladder assembly 20 also includes a percussion and vibration assembly 38, a body rotation assembly 40, and a foot rotation assembly 42. The percussion and vibration assembly 38 includes inflatable bladders 39 configured to apply percussion and/or vibration therapy to a patient supported on the mattress 12 to dislodge fluid in the patient's lungs or for other therapeutic purposes. The body rotation assembly 40 includes a left and a right working bladder 44, 45 and a left and a right turn bladder 46, 47. The bladders 44, 45, 46, 47 of the body rotation assembly 40 are configured to inflate and deflate to apply rotation therapy to a patient supported on the mattress 12 and to rotate the patient for linen changes or the like. The foot rotation assembly 42 includes a number of bladders 43 configured to inflate and deflate to apply rotation therapy to a patient's feet when the patient is supported on the mattress 12.

The air bladder assembly 20 also includes a lower support 51, a number of side bolsters 53, and a number of locating pads 55. The lower support 51 includes a head support 57 located to underlie and support the head cushion 30 of the air bladder assembly 20. The side bolsters 53 are illustratively made from foam and are arranged to fill the space between the mattress 12 and the frame 14 when the mattress 12 is supported on the frame 14. The locating pads 55 are coupled to the side bolsters 53 and are located to engage the frame 14 to locate the mattress 12 on the frame 14.

Referring to FIGS. 4 and 5, the frame 14 is configurable so that a patient supported on the bed 10 can be supported in a variety of positions as shown in FIGS. 4 and 5. The frame 14 includes a lower frame 48, an upper frame 50, and a pivotable deck 52. The upper frame 50 is supported over the lower frame 48 by a pair of arms 54, 56 as shown in FIG. 4. The pair of arms 54, 56 pivot to move the upper frame 50 relative to the lower frame 48 as shown in FIG. 5. The deck 52 is coupled to the upper frame 50 and is movable relative to the upper frame 50.

The deck 52 is movable to a number of predetermined configurations and illustratively includes a head deck section 58, a seat deck section 60, a thigh deck section 62, and a foot deck section 64 as shown in FIG. 5. The head deck section 58 is pivotably coupled to the seat deck section 60 and moves between a flat position and a number of inclined positions. When the head deck section 58 is in the inclined position, an angle $\alpha$ is formed between the head deck section 58 and the upper frame 50 as shown in FIG. 5. The seat deck section 60 is coupled to the upper frame 50 and moves therewith. The thigh deck section 62 is pivotably coupled to the seat deck section 60 and is spaced apart from the head deck section 58. The foot deck section 64 is pivotably coupled to the thigh deck section 62 and extends out from the upper frame 50.

The control system 22 of the bed 10 is shown diagrammatically in FIG. 6. The control system 22 includes an air system 66, deck drives 68, a controller 70, a user interface 72, and a transceiver 73. The air system 66 is operable to inflate or deflate the bladders of the mattress 12 to change the pressure profile of the mattress 12. The deck drives 68 are configured to move the head deck section 58, the thigh deck section 62, and the foot deck section 64 so that the deck 52 is movable among a variety of configurations. The controller 70 includes a memory 74 for storing instructions and data, a timer 75, and a processor 76 for executing instructions stored in the memory 74 and for writing additional data to the memory 74. The controller 70 is electrically coupled to the air system 66 and the deck drives 68 to direct operation of the air system 66 and the deck drives 68.

The user interface 72 and the transceiver 73 are also electrically coupled to the controller 70. The user interface 72 illustratively includes a touch-sensitive display 78 for displaying and receiving information and a keypad input 80 for receiving inputs from the user. In the illustrative embodiment, the user interface 72 is coupled to the siderails 21 of the bed 10 as shown in FIG. 1. The user interface 72 is operable to control entertainment devices such as televisions and radios, to operate the air system 66 to increase or decrease the firmness/pressure in the mattress 12, and to change the configuration of the deck 52.

The transceiver 73 is configured to transmit and receive information over a network. The network may use any of a number of hardware and communications protocols. In some embodiments, the network is configured as a peer-to-peer network. In other embodiments, the network may be configured in a master and slave configuration. In other embodiments, the transceiver 73 may be replaced by separate transmitters and receivers. The transceiver 73 may also be a wired device coupled to a network as is known in the art.

The control system 22 also has a number of sensors for detecting information about a patient supported on the bed 10 as shown diagrammatically in FIG. 6. The control system 22 includes pressure sensors 131, 133, 135, 137, a plurality of position sensors 82, and a plurality of load cells 84 each electrically coupled to the controller 70. The pressure sensors 131, 133, 135, 137 are configured to detect the pressure in the bladders 31, 33, 35, and 37 of the air bladder assembly 20, respectively. The position sensors 82 are illustratively accelerometers (not shown) and contact switches (not shown). In other embodiments, other switches or sensors may be used including non-contact proximity switches as well as potentiometers, for example. The accelerometers (not shown) are coupled to the deck sections 58, 60, 62, 64 and are configured to measure the angle of each deck sections 58, 60, 62, 64 relative gravity. Accelerometers may also be used to determine the tilt of the upper frame 50. The contact switches (not shown) are coupled to the siderails 21 and are configured to detect if the siderails 21 are in the blocking position or the exit position. The load cells 84 are illustratively coupled between the deck 52 and the upper frame 50. The load cells 84 are configured to measure the weight of a patient supported on the bed 10.

The air system 66 includes a manifold 86, an exhaust 88, and a source of pressurized air 90 as shown in FIG. 6. The manifold 86 is coupled to each of the bladders 31, 33, 35, 37, the exhaust 88, and the source of pressurized air 90. The exhaust 88 is in open fluid communication with the atmosphere around the bed 10. The source of pressurized air 90 is illustratively a compressor but in other embodiments may be a blower, an air tank, or another source of pressurized air.

The manifold 86 includes a number of valves (not shown) and is configured to selectively couple each bladder 31, 33, 35, 37 to the exhaust 88, the source of pressurized air 90, or to close the bladder 31, 33, 35, 37. When the manifold 86 is operated to couple a bladder 31, 33, 35, 37 to the exhaust 88, the bladder 31, 33, 35, 37 deflates so that the pressure in the bladder 31, 33, 35, 37 is reduced. When the manifold 86 is operated to couple a bladder 31, 33, 35, 37 to the source of pressurized air 90, the bladder 31, 33, 35, 37 inflates so that pressure in the bladder 31, 33, 35, 37 is increased. When the manifold 86 is operated to close the bladder 31, 33, 35, 37 the pressure in the bladder 31, 33, 35, 37 is substantially maintained unless a patient supported on the bladders 31, 33, 35, 37 shifts the weight supported by the bladder 31, 33, 35, 37.

Figure 7:
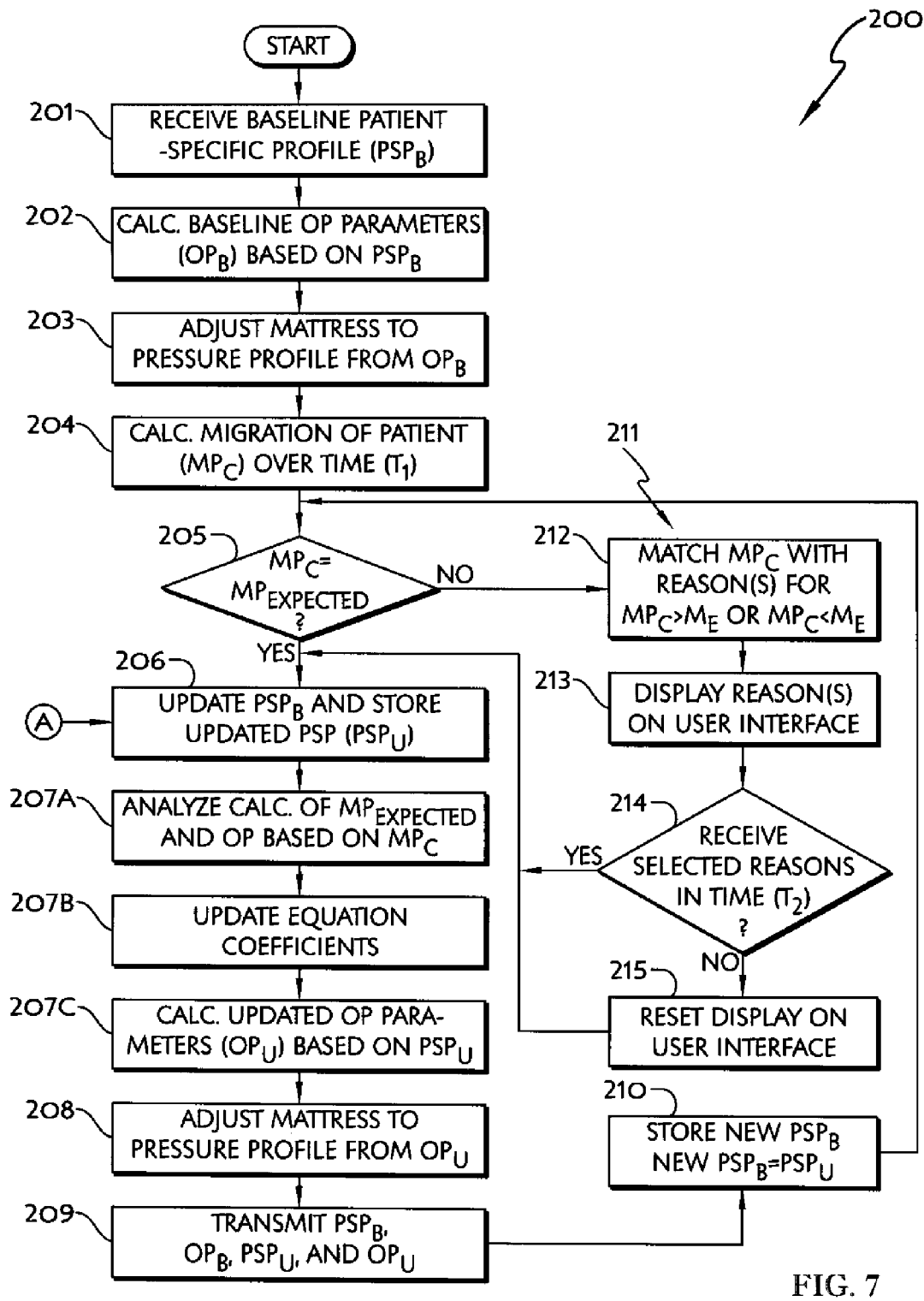
FIG. 7 is a diagram showing a routine performed by the control system of the patient-support apparatus.

Referring now to FIG. 7, a routine 200 for setting operating parameters of the bed 10 to reduce patient migration toward the foot end 18 of the bed 10 is performed by the controller 70 as shown. In step 201, the controller 70 retrieves a baseline patient-specific profile including information specific to a patient supported on the bed 10. The baseline patient-specific profile is illustratively retrieved from the memory 74 of the controller 70. In some embodiments, information included in the baseline patient-specific profile may be received by the transceiver 73 from an external data source such as an EMR (electronic medical record), input via the input 80 of the user interface 72, or detected by one or more of the sensors 131, 133, 135, 137, 82, 84 coupled to the controller 70.

The patient-specific profile of a patient includes one or more pieces of information about the patient supported on the bed 10. Information about the patient may include age, sex, weight, height, and the like. In the illustrative embodiment, calculated information about patient outcomes is also included in the patient-specific profile. Calculated information about patient outcomes include, for example, rates of patient migration toward the foot end 18 of the bed 10, patient mobility factors, and patient restlessness factors. Other information about the patient may also be included in the patient-specific profile such as caregiver assessed skin condition factors, caregiver assessed acuity factors, patient disorders, patient ailments, and time of therapy application (rotation, percussion, and/or vibration).

In the illustrative embodiment, the rate of patient migration toward the foot end 18 of the bed 10 is calculated based on the determined position of the patient on the bed 10 over time. In the illustrative embodiment, patient position is determined by pressures detected in the bladders 31, 33, 35, 37 of the air bladder assembly 20 and/or by weight distribution detected by the load cells 84. An illustrative method of determining patient position is more fully described in U.S. Patent Publication No. 2008-0189865, which is hereby incorporated by reference. In other embodiments, the position of a patient may be determined as described in U.S. Pat. No. 6,822,571, U.S. Pat. No. 7,253,366, or U.S. Pat. No. 6,208,250, each hereby incorporated by reference herein.

The patient mobility factor is illustratively calculated based on the number of times the patient is determined to be out of the bed 10, as indicated by the load cells 84, and on the amount of time the patient spends in an inclined position, as indicated by the position sensors 82. The patient restlessness factor is illustratively calculated based on the number of times a patient adjusts the firmness of the mattress 12, as indicated by the user interface 72 and the pressure sensors 131, 133, 135, 137, and the number of times a patient adjusts his position on the bed 10, as indicated by the pressure sensors 131, 133, 135, 137. In some embodiments, other inputs contribute to the calculation of the patient mobility factor and the patient restlessness factor.

Moving to step 202 of routine 200, the controller 70 calculates a series of baseline operating parameters for the bed 10 illustratively including target pressure profiles for the bladders 31, 33, 35, 37 corresponding to different positions of the deck 52, maximum and minimum allowed pressure ranges for the bladders 31, 33, 35, 37 at each position of the deck 52, and allowed configurations of the deck 52. Each operating parameter is calculated in a multivariable algorithm based on the available patient-specific information each multiplied by a respective coefficient. During an initial performance of the routine 200, the operating parameters for the bed 10 may be based on a patient-specific profile that does not include calculated patient-specific information to indicate that they are unavailable.

In an illustrative example, the multivariable equation for one operating parameter is of the form:

$$OP_A = C_{OP1}PF_1 + C_{OP2}PF_2 + C_{OP3}PF_3 \ldots$$

In the illustrative form, OP is one operating parameter of the bed 10, $C_{OP}$ is a coefficient for calculating operating parameters, and PF is a patient factor from the patient-specific profile. Some of the patient factors from the patient-specific profile are constant in response to bed operating parameters. For example, a patient's age, sex, and weight are constant. Other patient factors are dependent on changes in bed operating parameters. For example, rates of patient migration toward the foot end 18 of the bed 10, patient mobility factors, and patient restlessness factors may vary over time depending on the operating parameters of the bed 10.

In step 203 of routine 200, the controller 70 adjusts the pressures in the mattress 12 to match the target pressures for the current configuration of the frame 14 included in the baseline operating parameters by operating the air system 66 included in the control system 22. The controller 70 also begins controlling to the maximum and minimum pressure ranges for the bladders 31, 33, 35, 37 at each position of the deck 52 and begins enforcing the allowed configurations of the deck 52 (moving the deck 52 if currently outside the allowed configurations). In some embodiments, available pressure ranges and/or deck configurations are illuminated or displayed on the user interface 72 and unavailable pressure ranges and/or deck configurations are darkened or removed from the user interface 72.

In step 204, the controller 70 calculates the migration of the patient toward the foot end 18 of the bed 10 over a predetermined amount of time. Following the calculation of migration, the calculated migration of the patient is compared to an expected patient outcome range corresponding to a range of migration values in decision step 205. The expected patient outcome corresponding to migration is illustratively determined using a multivariable equation of the form:

$$MP_{EXPECTED}=C_{MP1}PF_1+C_{MP2}PF_2+C_{MP3}PF_3\ldots C_{MPA}OP_A+C_{MPB}OP_B\ldots$$

In the illustrative form, $MP_{EXPECTED}$ is the expected amount of patient migration, $C_{MP}$ is a coefficient for calculating migration of the patient, PF is a patient factor from the patient-specific profile, and OP is an operating parameter of the bed 10. The upper and lower ends of the expected patient migration outcome range may be determined to be a statistically significant number of values above and below the expected value. In other embodiments, two equations may be used to establish upper and lower ends of the range.

If the migration calculated is within the range expected, the routine 200 proceeds to step 206 and updates the patient-specific profile to include the calculated amount of patient migration and stores the updated patient-specific profile in the memory 74. Once the updated patient-specific profile is stored in the memory 74, the controller 70 performs step 207A performing a multivariable analysis, such as regression analysis, based on the equation used to calculate the expected patient migration and the actual patient migration to learn which operating parameters are likely to affect the measured patient outcome. Then, in step 207B, the controller 70 updates the coefficients used to determine operating parameters and the expected patient migration outcome based on the learned information about the specific patient. Thus, the algorithm learns and responds to the specific patient by updating the coefficients.

Because the algorithm adapts to patient response, the updated set of operating parameters may differ from the baseline operating parameters even though the migration calculated is equal to an expected migration value. For instance, the updated set of operating parameters may allow a wider range of selectable pressures in the mattress 12 or allow additional configurations of the frame 14 to be selected by the patient or the caregiver if the patient's migration is within the expected migration values for a set period of time. Additionally, the updated set of operating parameters may be adjusted to affect changes in other patient outcomes, for example minimizing patient restlessness, maximizing patient mobility, or reducing the likelihood of bed sores by reducing interference pressures.

Because one or more patient outcomes may be interdependent, the controller 70 modifies operating parameters to optimize the impact on the patient. For example, a highly mobile patient has a reduced opportunity for development of bed sores because the patient is not likely to be bedridden. If a patient is mobile, but restless while in the bed, the algorithm may infer that the mattress pressures are uncomfortable to the patient and the restlessness is an artifact of discomfort. In such a situation, the algorithm will optimize the pressure for comfort and not interface pressure control.

In step 207C, the controller calculates updated operating parameters based on the updated multivariable equation. In step 208 of routine 200, the controller 70 adjusts the pressures in the mattress 12 to match the target pressures for the current configuration of the frame 14 included in the updated operating parameters by operating the air system 66 included in the control system 22. The controller 70 also begins enforcing updated maximum and minimum pressure ranges for the bladders 31, 33, 35, 37 at each position of the deck 52 and begins enforcing the allowed configurations of the deck 52 (moving the deck 52 if currently outside the allowed configurations). In some embodiments, newly available pressure ranges and/or deck configurations are illuminated or displayed on the user interface 72 and newly unavailable pressure ranges and/or deck configurations are darkened or removed from the user interface 72 to provide an indication of availability.

In step 209, the baseline patient-specific profile, the baseline operating parameters, the updated patient-specific profile, and the updated operating parameters are transmitted by the transceiver 73. The transmitted information may be received by an external data center where it may be stored for additional processing and analysis. In other embodiments, the transmitted information may be stored in the memory 74 of the bed 10 or transmitted to another data storage device for additional analysis.

In step 210 the updated patient-specific profile is stored as the new baseline patient-specific profile completing an iteration of the routine 200. After completing step 210, the routine 200 loops back to step 204 to calculate migration of the patient toward the foot end 18 of the bed 10 while the bed 10 operates using operation parameters corresponding to the new baseline patient-specific profile. By repeating steps 204 through 210 of routine 200 with differing sets of operating parameters in a design of experiments, the controller 70 learns about a patient supported on the bed 10 and can refine equation coefficients and operating parameters to obtain a number of desired patient outcomes such as minimized migration toward the foot end 18 of the bed 10, minimized patient restlessness, maximized patient mobility, and minimized chance of bed sores.

If the migration calculated in step 204 falls outside of range of migration values expected in decision step 205, then the routine 200 enters a subroutine 211. In step 212 of subroutine 211, the controller 70 compares the baseline patient-specific profile and calculated amount of patient migration to a number of likely reasons for the difference. For example, if the calculated migration exceeds the expected range of migration values, the patient may have been recently sedated or medicated, may have been sleeping during normal waking hours, or may have a disorder or ailment consistent with excessive migration toward the foot end 18 of the bed 10. Alternately, if the calculated migration is below the expected range of migration values, the patient may have been coming out of a sedated state, may have been awake during normal sleeping hours, or may have a disorder or ailment consistent with lack of migration toward the foot end 18 of the bed 10.

When the controller 70 determines the likely reason or reasons for the calculated migration values to fall outside the expected range, the controller 70 proceeds to step 213 of subroutine 211 and directs the display 78 of the user interface 72 to show the reason(s) for review by a caregiver, a patient, or other user and prompts the user to select the applicable reason. In decision step 214, the controller 70 determines if it has received an input indicating a selection of one or more of the reasons from the input 80 of the user interface 72 during a predetermined response time. If the controller 70 has received an input during the response time, the controller 70 exits the subroutine 211 and proceeds to step 206 updating the baseline patient-specific profile with information corresponding to both the calculated amount of patient migration and the reasons selected explaining the unexpected migration. If the controller 70 has not received an input during the response time, the controller 70 proceeds to step 215 and resets the display 78 of the user interface 72 before exiting the subroutine 211 and proceeding to step 206 to update the baseline patient-specific profile with the calculated amount of patient migration. By including reasons for unexpected migration in the patient-specific profile, the controller 70 can identify patient conditions relevant to the calculation of operating parameters (such as restless leg syndrome, bed sores, and the like) and can disregard information corresponding to incidental factors.

Turning now to FIG. 7, routine 200 also includes subroutine 220 for optimizing the patient mobility outcomes while maintaining patient migration outcome within the expected range. In step 221, the controller 70 calculates a mobility factor for a patient supported on the bed 10. The calculated mobility factor is illustratively based on the number of times the patient exits/enters the bed 10 (indicated by the load cells 84 and/or by the raising and lowering of the siderails 21). In other embodiments, other data input through the user interface 72 or received by the transceiver 73 may be used to calculate mobility factor.

In decision step 222, the controller 70 compares the calculated mobility factor to an expected (optimized) range of mobility factor values. If the calculated mobility factor is equal to an expected mobility factor value (the expected value illustratively calculated using a multivariable equation similar to the equation used to calculate expected patient migration), then the subroutine 220 advances to step 206 of routine 200 so that the baseline patient-specific profile is updated to include the calculated mobility factor before looping back to repeat subroutine 220. If the calculated mobility factor determined in decision step 222 is not equal to one of the expected mobility factor values, the subroutine 220 advances to step 223.

In step 223, the controller 70 compares the baseline patient-specific profile and calculated mobility factor to a number of likely reasons for the difference between the calculated mobility factor and the expected mobility factor. For example, the calculated mobility factor may be greater than or less than the expected range of mobility factors in response to the patient having an improving/deteriorating acuity score, responding to diet or medication, having been moved a number of times for tests or procedures, or having trouble sitting up on a low pressure or "soft" mattress 12.

When the controller 70 determines the likely reason or reasons for the calculated migration values to fall outside the expected range, the controller 70 proceeds to step 224 of subroutine 220 and directs the display 78 of the user interface 72 to show the reason(s) for review by a caregiver, a patient, or other user and prompts the user to select the applicable reason. In decision step 225, the controller 70 determines if it has received an input indicating a selection of one or more of the reasons from the user interface 72 during a predetermined response time. If the controller 70 has received a selection during the response time, the controller 70 proceeds to step 206 of routine 200 and updates the baseline patient-specific profile with information corresponding to both the calculated mobility factor and the reasons selected for the unexpected mobility. If the controller 70 has not received an input during the response time, the controller 70 proceeds to step 226 and resets the display 78 of the user interface 72 before moving on to step 206 of routine 200 and updating the baseline patient-specific profile with the calculated mobility factor outside the expected range.

When calculated mobility factors outside the expected range are included in an updated patient-specific profile, the controller 70 may modify parameters in the updated operational parameters calculated in step 207 in an effort to optimize the mobility factor controlling for an expected amount of migration toward the foot end 18 of the bed 10. For example, the updated operational parameters may include a target pressure profile with an increased pressure in the seat cushion 34 of the mattress 12 to make exiting the bed 10 easier for a patient thereby encouraging an increase in the calculated mobility factor. However, if mobility factors outside the expected range correspond to reasons external to the bed 10 (such as movements from the bed for tests) selected by a caregiver, user, or patient, then the controller 70 may ignore the calculated mobility factor.

Figures 8, 9:
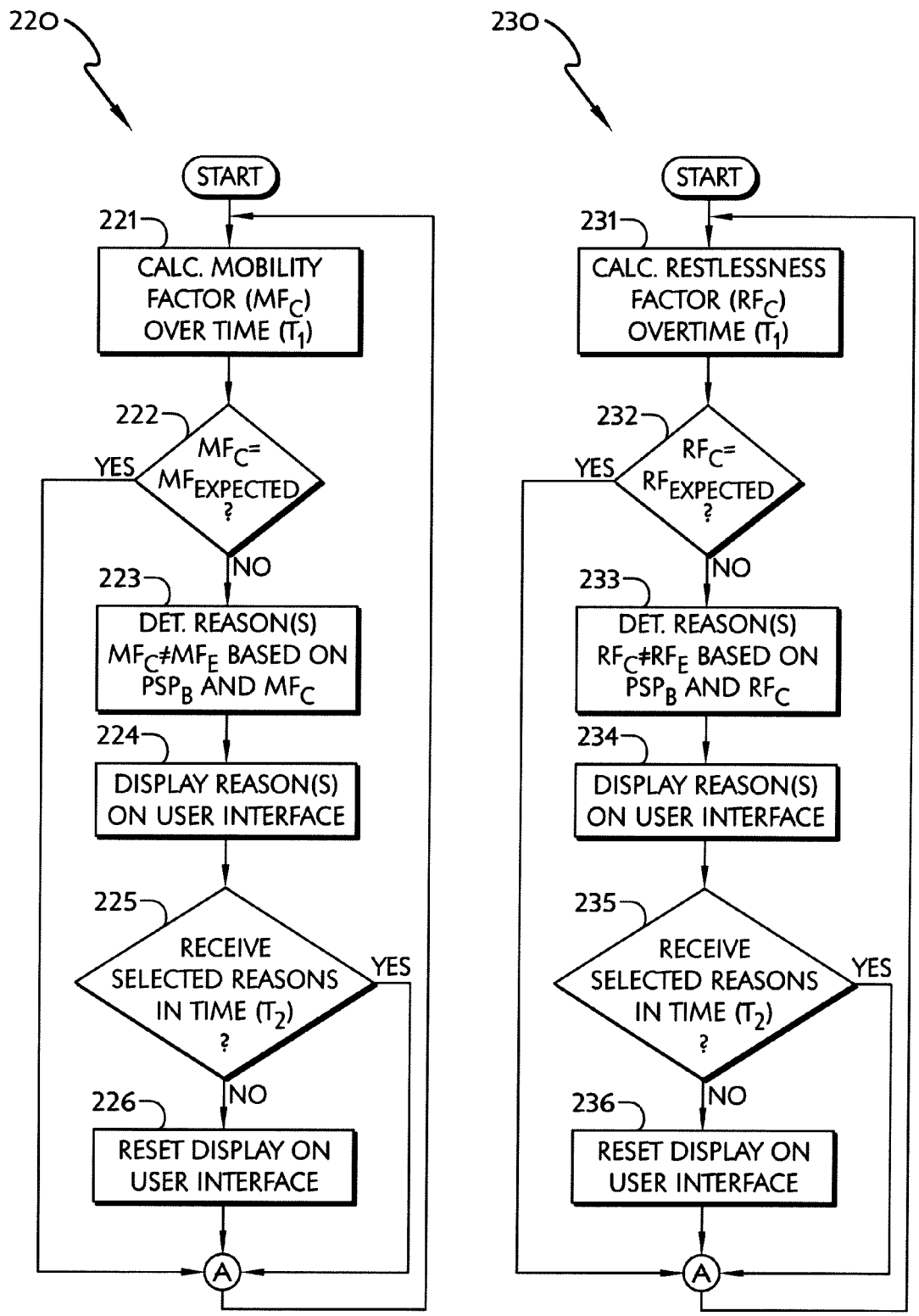
FIG. 8 is a diagram showing a subroutine of the routine shown in FIG. 7 performed by the control system of the patient-support apparatus.
FIG. 9 is a diagram showing a subroutine of the routine shown in FIG. 7 performed by the control system of the patient-support apparatus.

Referring now to FIG. 8, routine 200 also includes subroutine 230 for optimizing the patient restlessness outcomes while maintaining patient migration outcome within the expected range. In step 231, the controller 70 calculates a restlessness factor for a patient supported on the bed 10. The calculated restlessness factor is illustratively based on a sensed in-bed movement during normal sleeping hours using information from the load cells 84 indicating movement. In some embodiments, the restlessness calculation may include a parameter corresponding to the number of times a patient repositions himself as indicated by adjustments to the bladders 31, 33, 35, 37 of the mattress 12 to maintain a pressure profile. In the illustrative embodiment, the restlessness calculation includes the amount of time the frame 14 is in an inclined position and the frequency of frame movement as measured by the position sensors 82. Further, the illustrative restlessness calculation includes the number of times a patient adjusts entertainment devices (not shown) using the user interface 72. In other embodiments, additional parameters input through the user interface 72 or received by the transceiver 73 may be used to calculate restlessness factor.

By detecting the times of patient movement, the frequency of bed adjustment, and the times of entertainment device use it can be deduced whether or not a patient is resting in one place consistent with restful sleep. Patient restlessness is interdependent with other patient outcomes and therefore modifying operating parameters to optimize patient restlessness may impact other patient outcomes. For example, it is known that low mattress pressures can decrease restlessness. However, very low mattresses pressures can depress mobility by making patient bed exits harder to accomplish. If it is known that a patient is highly mobile and performs multiple bed exits per day, the algorithm may infer that very low mattress pressures are unlikely to compromise mobility when pressure is reduced. In such a situation, the algorithm will optimize the pressures to reduce restlessness by reducing mattress pressures and will not optimize for mobility.

In decision step 232, the controller 70 compares the calculated restlessness factor to an expected (optimized) range of restlessness factor values. If the calculated restlessness factor is equal to an expected restlessness factor value (the expected value illustratively calculated using a multivariable equation similar to the equation used to calculate expected patient migration), then the subroutine 230 sends information to step 206 of routine 200 so that the baseline patient-specific profile is updated to include the calculated restlessness factor before looping back around to repeat subroutine 230. If the calculated restlessness factor is determined in decision step 232 to not equal to one of the expected restlessness factor values, the subroutine 230 advances to step 233.

In step 233, the controller 70 compares the baseline patient-specific profile and calculated restlessness factor to a number of likely reasons for the difference between the calculated restlessness factor and the expected restlessness factor. For example, the calculated restlessness factor may be greater than or less than the expected range of restlessness factors because of recent patient surgery, a rash or other skin condition, or the patient being uncomfortable on the mattress 12.

When the controller 70 determines the likely reason or reasons for the calculated restlessness values to fall outside the expected range, the controller 70 proceeds to step 234 of subroutine 230 and directs the display 78 of the user interface 72 to display the reason(s) for review by a caregiver, a patient, or other user. In decision step 235, the controller 70 determines if it has received an input indicating a selection of one or more of the reasons from the user interface 72 during a predetermined response time. If the controller 70 has received an input during the response time, the controller 70 proceeds to step 206 of routine 200 and updates the baseline patient-specific profile with information corresponding to both the calculated restlessness factor and the reasons selected for the unexpected restlessness before looping to repeat subroutine 230. If the controller 70 has not received an input during the response time, the controller 70 proceeds to step 236 and resets the display 78 of the user interface 72 before moving on to step 206 of routine 200 where the controller 70 updates the baseline patient-specific profile with the calculated restlessness factor outside the expected range before looping to repeat subroutine 230.

When calculated restlessness factors outside the expected range are included in an updated patient-specific profile, the controller 70 may modify parameters in the updated operational parameters calculated in step 207 in an effort to optimize the restlessness factor while maintaining the expected amount of migration toward the foot end 18 of the bed 10. For example, the updated operational parameters may include a target pressure profile with a decreased pressure in the foot cushion 36 of the mattress 12 to make the bed 10 more comfortable for a patient thereby encouraging a decrease in the calculated restlessness factor. However, if restlessness factors outside the expected range correspond to reasons external to the bed 10 (such as new medication) selected by a caregiver, user, or patient, then the controller 70 may ignore the calculated restlessness factor.

Additional subroutines can be implemented to optimize additional patient outcomes by updating operational parameters in response to unexpected (un-optimized) outcomes. For example, additional subroutines can optimize for low interface pressure between the mattress 12 and a patient. Using a multivariable analysis, each patient outcome can be optimized while controlling for other patient outcomes.

Referring now to FIG. 9, a data analysis system 300 for collecting and analyzing data collected from a number of beds 10A, 10B, 10C, 10D, 10E, 10F, 10G, 10H, 10I is shown. Each bed 10A, 10B, 10C, 10D, 10E, 10F, 10G, 10H, 10I is substantially similar to the bed 10 described above. In other embodiments, a number of different bed models may be incorporated into the data analysis system 300. The data analysis system 300 illustratively includes a number of hospital networks 302A, 302B, 302C and a central information center 304. Each of the hospital networks 302A, 302B, 302C are in two way communication with the central information center 304. The central information center 304 is illustratively a number of real or virtualized computer servers coupled to a communication network and configured to store and process data.

Each hospital network 302A, 302B, 302C may be located in a single building or may be spread across a number of hospital buildings, administrative buildings, clinics, pharmacies, and/or nursing homes. Illustratively, each hospital network 302A, 302B, 302C is substantially similar and therefore only hospital network 302A is described further. The hospital network 302A illustratively includes a number of beds 10A, 10B, 10C and a hospital information system 306A. Each bed 10A, 10B, 10C is in two way communication with the hospital information system 306A via transceiver 73. The hospital information system 306 is illustratively a number of real or virtualized computer servers coupled to a communication network and configured to store and process data.

Figure 10:
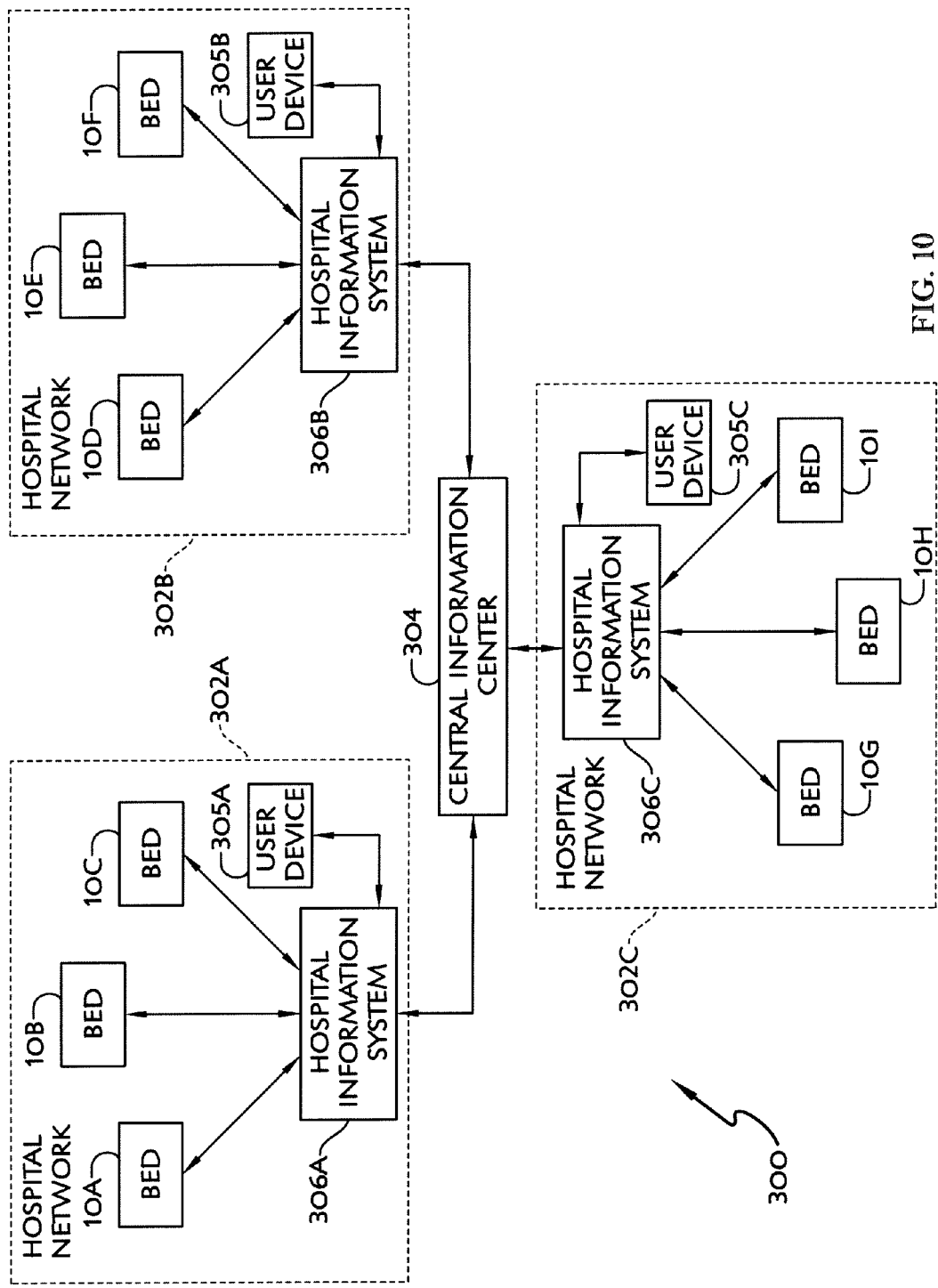
FIG. 10 is a diagrammatic view of a data analysis system including a number of patient-support apparatuses located in hospital networks, the data analysis system configured to collect information from each of the patient-support apparatuses and to analyze the information to generate algorithms for calculating operating parameters for the patient-support apparatuses.
Figure 11:
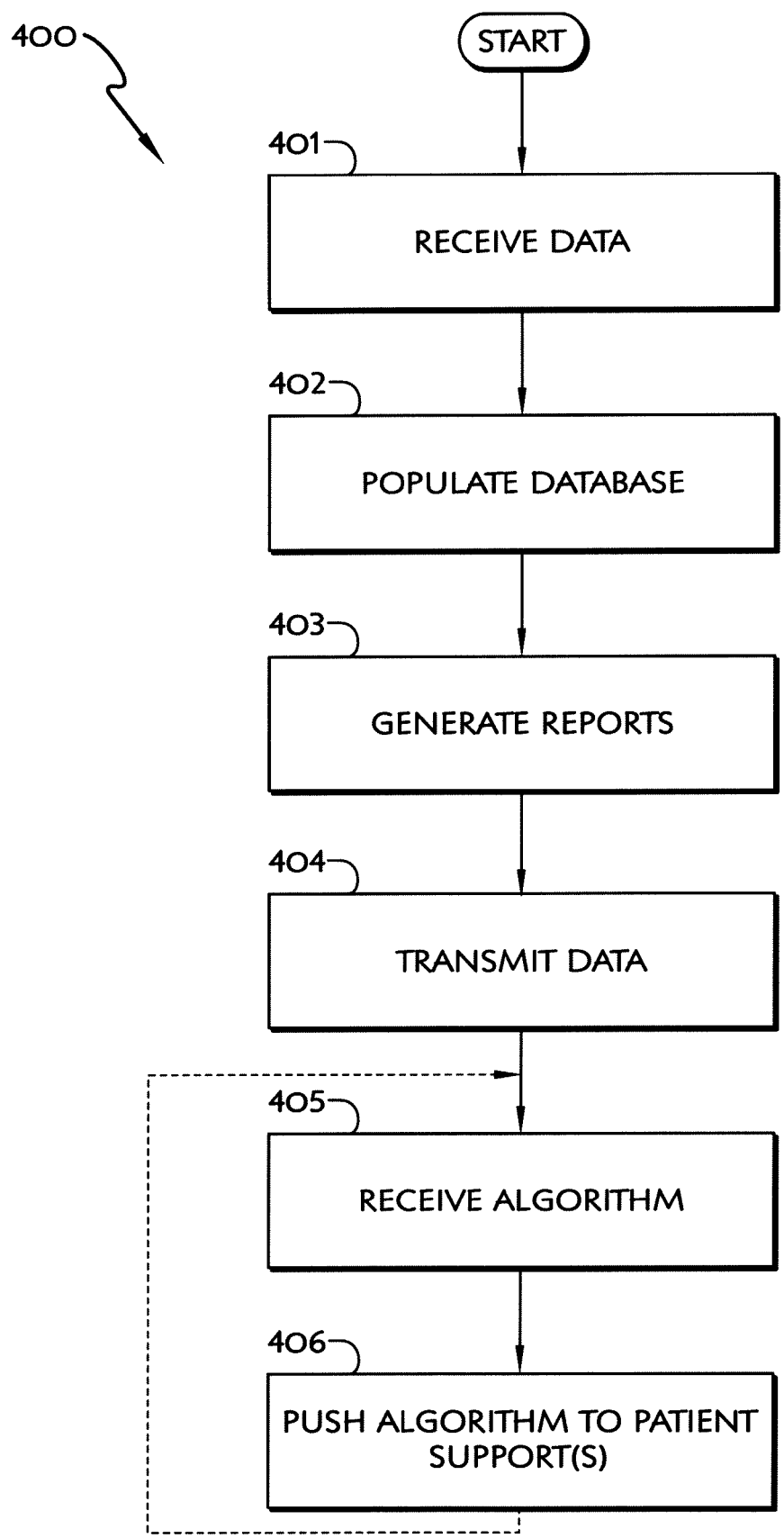
FIG. 11 is a flow chart showing a routine performed by a hospital information system included in each of the hospital networks of FIG. 10.
Figure 12:
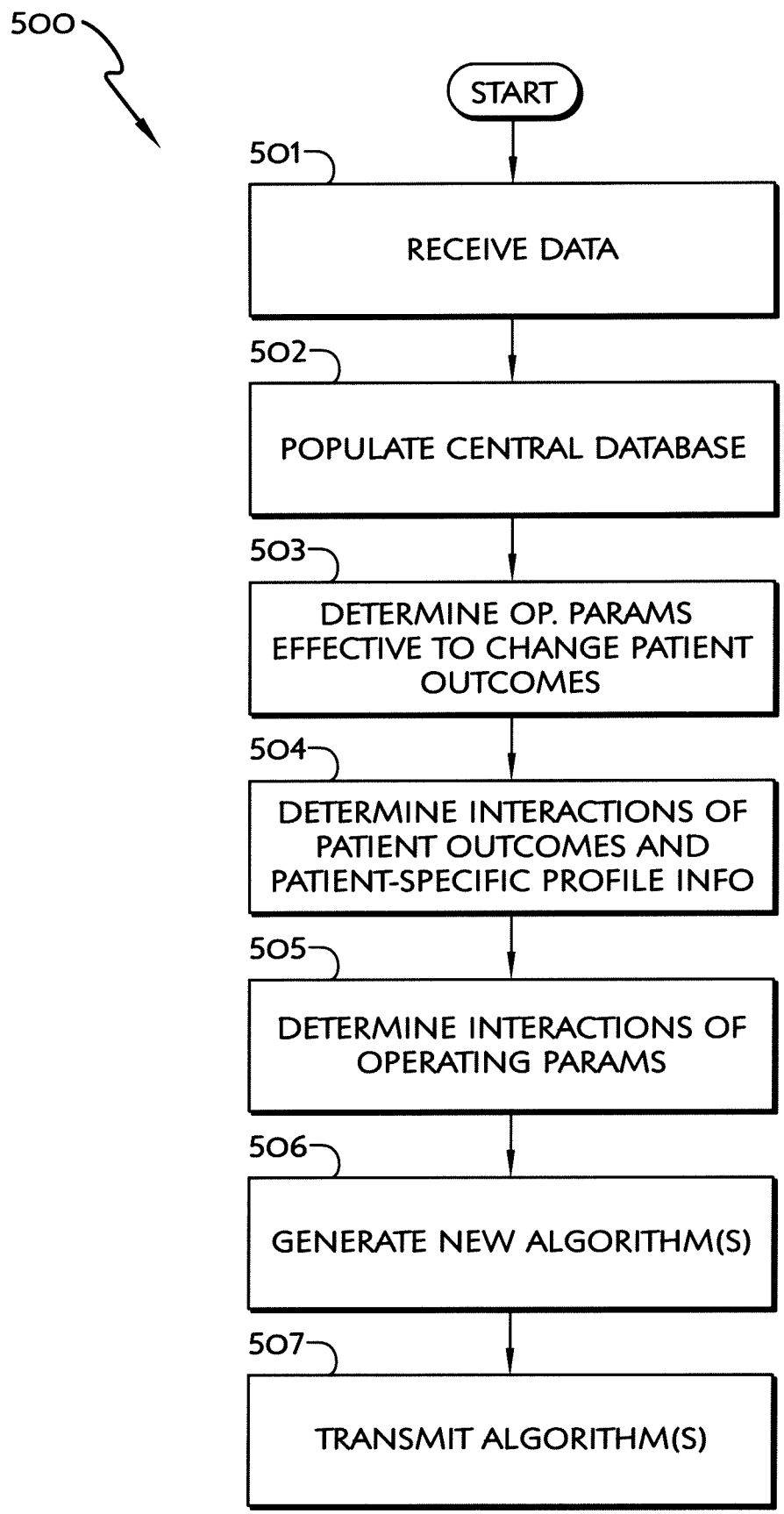
FIG. 12 is a flow chart showing a routine performed by a central information center included in the data analysis system of FIG. 10.

When each bed 10A, 10B, 10C performs routine 200 to set operating parameters, each bed 10 transmits patient information and corresponding operating parameter information in step 209 of the routine 200. In response to the beds 10A, 10B, 10C transmitting information, the hospital information system 306A performs a routine 400 to process the information as shown in FIG. 10. In step 401, the hospital information system 306A receives the patient information and corresponding operating parameter information from the beds 10A, 10B, 10C. Next, the hospital information system 306A populates a database including information from a number of beds 10 included in the hospital network 302A as shown in step 402.

In step 403, the hospital information system 306A generates reports including information about patients in the hospital network 302A including migration, patient restlessness, patient mobility or other patient outcomes based on data in the populated database. Additionally, the hospital information system 306A compiles reports including information about caregiver attentiveness to prompts displayed on the user interface 72. The compiled reports are available to be retrieved by users of the hospital information system 306A on user devices 305A in communication with the hospital information system 306A such as personal computers, PDAs, mobile phones, or on other user interfaces around the hospital network 302A.

In step 404, the hospital information system 306A communicates with the central information center 304 to transmit data from the populated database to the central information center 304. In step 405, the hospital information system 306A receives new algorithms for calculating operating parameters of the beds 10A, 10B, 10C. The new algorithms are adapted based on the collective information acquired from multiple hospitals. Once the new algorithms are received in step 405, the hospital information system 306 populates the new algorithms on each controller 70 of each of the beds 10A, 10B, 10C in the hospital network 302A as shown in step 406 of routine 400. Steps 405 and 406 of routine 400 may be repeated at regular intervals to ensure that the beds 10A, 10B, 10C are updated with the newest algorithms for setting operational parameters.

The central information center 304 performs a routine 500 to analyze the data collected from beds 10A, 10B, 10C, 10D, 10E, 10F, 10G, 10H, 10I and to generate new algorithms for setting operating parameters for the beds 10A, 10B, 10C, 10D, 10E, 10F, 10G, 10H, 10I. Routine 500 uses multivariate analysis of the variance detected in the calculated patient outcomes to adjust the coefficients used to calculate expected outcomes for the beds 10A, 10B, 10C, 10D, 10E, 10F, 10G, 10H, 10I.

In step 501 of routine 500, the central information center 304 receives data from each hospital information system 306A, 306B, 306C. Next, in step 502, the central information center 304 populates a central database with patient information and corresponding applied operating parameters. Using data from the populated central database, the central information center 304 of the illustrative embodiment applies multivariate analytics, such as regression analysis, and multivariate statistical analysis to determine what operating parameters (independent variables) are likely to have effects on the measured or calculated patient outcomes (dependent variables) as shown in step 503. Because the central information center 304 analyzes data from a large number of beds with different patient specific information, the analysis of effective operating parameters may be more robust than a single bed 10 or single hospital network 302A, 302B, 302C analysis.

In step 504, the central information center 304 determines interactions among the patient-specific profiles and the calculated patient outcomes (independent variables). Comparing large numbers of patient-specific profiles with different amounts of information and calculated patient outcomes allows the central information center 304 to identify trends among certain types of patients and to identify potential reasons for unexpected patient responses. For example, if a patient-specific profile does not indicate that a patient is incontinent but the patient's outcomes such as sustained high mobility and restlessness are consistent with the patient outcomes of other patients whose profile include incontinence, the central information center 304 can associate incontinence as a selectable reason for unexpected outcomes for future patients with a similar profile.

In step 505, the central information center 304 also determines interactions among the operating parameters. Comparing large numbers of operating parameters the central information center 304 is able to identify combinations of parameters that resulted in expected, optimized outcomes. From these analyses, the central information center 304 develops a master profile for how patient outcomes are affected when a patient is subjected to different operating parameters.

In step 506, the central information center 304 generates new algorithms for calculating operating parameters based on patient-specific profile information and new algorithms for calculating expected patient outcomes. The new algorithms are then transmitted back to each bed 10A, 10B, 10C, 10D, 10E, 10F, 10G, 10H, 10I through the hospital information systems 306A, 306B, 306C in step 507. The new algorithms are applied when the controllers 70 of the beds 10A, 10B, 10C, 10D, 10E, 10F, 10G, 10H, 10I perform routine 200 to optimize patient outcomes.

In the illustrative embodiment, reception of new algorithms for calculating operating parameters is provided to each hospital network 302A, 302B, 302C as part of a subscription service. The subscription service is offered by the operator of the central information center 304. In other embodiments, each hospital information system 306A, 306B, 306C may be configured to use artificial intelligence to learn about individual patient reactions and to generate new algorithms for calculating updated operating parameters based on information from the hospital network 302A, 302B, 302C corresponding to the hospital information systems 306A, 306B, 306C.

The invention claimed is:

1. A patient-support apparatus comprising
   a source of pressurized air,
   a plurality of bladders coupled to the source of pressurized air,
   a plurality of pressure sensors configured to produce pressure signals indicative of air pressure within the plurality of bladders, and
   a controller in electrical communication with the source of pressurized air and the plurality of pressure sensors, the controller configured to
   receive a patient-specific profile,
   determine an expected first patient outcome over a time interval based on the patient-specific profile and an operating parameter of the patient-support apparatus,
   determine a set of patient-specific operating parameters including a set of target pressures for the plurality of bladders based on the patient-specific profile,
   determine an actual first patient outcome over the time interval based on the pressure signals,
   update the patient-specific operating parameters if the actual first patient outcome and the expected first patient outcome are different,
   update the patient-specific profile to include the first patient outcome, and
   adjust the pressures in the bladders to the target pressures.

2. The patient-support apparatus of claim 1, wherein the first outcome is an amount of patient migration toward a foot end of the plurality of bladders.

3. The patient-support apparatus of claim 2, wherein the controller determines a list of reasons based on the patient-specific profile when the actual first patient outcome is not equal to the expected first patient outcome.

4. The patient-support apparatus of claim 3, further comprising a display coupled to the controller, wherein the controller displays the list of reasons on the display.

5. The patient-support apparatus of claim 4, wherein the controller receives a selected reason from the list of reasons via an input coupled to the controller and updates the patient-specific profile to include the selected reason.

6. The patient-support apparatus of claim 1, wherein the controller determines an actual second patient outcome.

7. The patient-support apparatus of claim 6, wherein the controller updates the patient-specific profile to include the actual second patient outcome.

8. The patient-support apparatus of claim 6, wherein the controller updates the patient-specific operating parameters if the actual second outcome is not equal to an expected second outcome.

9. The patient-support apparatus of claim 1, wherein the expected first patient outcome is selected from a group consisting of: migration of a patient toward a foot end of the plurality of bladders, patient restlessness, patient mobility, and chance of bed sores.

10. The patient-support apparatus of claim 1, wherein the actual first patient outcome is selected from a group consisting of: migration of a patient toward a foot end of the plurality of bladders, patient restlessness, patient mobility, and chance of bed sores.

11. A patient-support apparatus comprising
a source of pressurized air,
a plurality of bladders coupled to the source of pressurized air,
a plurality of pressure sensors coupled to the plurality of bladders and configured to produce pressure signals indicative of air pressure within the plurality of bladders, and
a controller in electrical communication with the source of pressurized air and the plurality of pressure sensors, the controller configured to iteratively
determine an expected first patient outcome corresponding to the amount of migration of a patient toward a foot end of the plurality of bladders over a time interval based on the patient-specific profile and an operating parameter of the patient-support apparatus,
determine an actual first patient outcome corresponding to the amount of migration of a patient toward a foot end of the plurality of bladders over a time interval,
update a patient-specific profile to include at least one of the expected first patient outcome, the actual first patient outcome, and a difference between the expected first patient outcome and the actual first patient outcome,
determine a set of operating parameters based on the updated patient-specific profile, wherein the set of operating parameters includes a first set of target pressures for the plurality of bladders, and
adjust the pressures in the bladders to the first set of target pressures.

12. The patient-support apparatus of claim 11, further comprising a deck movable between a first configuration and a second configuration.

13. The patient-support apparatus of claim 12, wherein the operating parameters include a second set of target pressures for the plurality of bladders and the controller is configured to (i) adjust the pressures in the bladders to the first set of target pressures when the deck is in the first configuration and (ii) adjust the pressures in the bladders to the second set of target pressures when the deck is in the second configuration.

14. The patient-support apparatus of claim 12, wherein the operating parameters include a parameter set to allow or to prevent movement of the deck from the first configuration to the second configuration.

15. The patient-support apparatus of claim 11, further comprising a transceiver coupled to the controller, wherein the controller is configured to transmit the patient-specific profile and the operating parameters via the transceiver to an external information system.

16. The patient-support apparatus of claim 11, further comprising a transceiver coupled to the controller, wherein the controller receives an algorithm for determining the operating parameters based on the patient-specific profile via the transceiver.

17. The patient-support apparatus of claim 16, further comprising a transceiver coupled to the controller and configured to communicate with a hospital information system.

18. The patient-support apparatus of claim 17, wherein the controller is configured to send the updated patient-specific profile to the hospital information system via the transceiver.

19. The patient-support apparatus of claim 11, wherein during a first iteration of the instructions, the controller is configured to retrieve the patient-specific profile from an internal memory.

20. The patient-support apparatus of claim 19, wherein the patient-specific profile includes information corresponding to at least one of patient age, patient weight, patient height, and patient sex.

21. A patient-support apparatus comprising
a source of pressurized air,
a plurality of bladders coupled to the source of pressurized air,
a plurality of pressure sensors coupled to the plurality of bladders and configured to produce pressure signals indicative of air pressure within the plurality of bladders, and
a controller in electrical communication with the source of pressurized air and the plurality of pressure sensors, the controller configured to determine an expected first patient outcome corresponding to an amount of migration of a patient toward a foot end of the plurality of bladders over a time interval based on a patient-specific profile and an operating parameter of the patient-support apparatus and the controller is further configured to determine an actual first patient outcome corresponding to the amount of patient migration toward a foot end of the plurality of bladders over a time interval and to adjust target pressures for the plurality of bladders based on the actual first patient outcome.

22. The patient support apparatus of claim 21, wherein the controller is configured to determine an actual second patient outcome corresponding to an amount of patient migration toward a foot end of the plurality of bladders over a time interval after the adjustment of target pressures and to adjust target pressures for the plurality of bladders a second time based on the actual first patient outcome and the actual second patient outcome.

* * * * *